US011096885B2

(12) United States Patent
Lee et al.

(10) Patent No.: US 11,096,885 B2
(45) Date of Patent: Aug. 24, 2021

(54) COMPOSITION FOR ENHANCING SKIN ELASTICITY OR IMPROVING SKIN WRINKLES COMPRISING GINSENG CELL LYSATE

(71) Applicant: AMOREPACIFIC CORPORATION, Seoul (KR)

(72) Inventors: Eunjung Lee, Yongin-si (KR); Nok Hyun Park, Yongin-si (KR); Hyangtae Choi, Yongin-si (KR); Young Gyu Kang, Yongin-si (KR); Dong Hyun Kim, Yongin-si (KR); Yong Jin Kim, Yongin-si (KR)

(73) Assignee: AMOREPACIFIC CORPORATION, Seoul (KR)

(*) Notice: Subject to any disclaimer, the term of this patent is extended or adjusted under 35 U.S.C. 154(b) by 0 days.

(21) Appl. No.: 16/550,758

(22) Filed: Aug. 26, 2019

(65) Prior Publication Data

US 2020/0069566 A1 Mar. 5, 2020

(30) Foreign Application Priority Data

Aug. 29, 2018 (KR) ........................ 10-2018-0102056

(51) Int. Cl.

| | |
|---|---|
| ***A61K 36/00*** | (2006.01) |
| ***A61K 8/9789*** | (2017.01) |
| ***A61Q 19/08*** | (2006.01) |
| ***A61K 8/34*** | (2006.01) |

(52) U.S. Cl.
CPC ............ *A61K 8/9789* (2017.08); *A61K 8/345* (2013.01); *A61Q 19/08* (2013.01)

(58) Field of Classification Search
None
See application file for complete search history.

(56) References Cited

U.S. PATENT DOCUMENTS

| | | | | |
|---|---|---|---|---|
| 9,095,532 | B2 | 8/2015 | Jang et al. | |
| 2011/0085996 | A1 | 4/2011 | Yeom et al. | |
| 2013/0302287 | A1* | 11/2013 | Jang ........................ | A61P 17/00 424/93.7 |

FOREIGN PATENT DOCUMENTS

| | | | |
|---|---|---|---|
| CN | 107648170 | A * | 2/2018 |
| KR | 20090073304 | A | 7/2009 |
| KR | 20090130801 | A | 12/2009 |
| KR | 1020110123934 | A | 11/2011 |
| KR | 101126315 | B1 | 3/2012 |
| KR | 101676607 | A | 11/2016 |
| KR | 1888145 | B1 * | 8/2018 |

OTHER PUBLICATIONS

Gwang-Tae Choe, "Production of Ginsenoside by Ginseng Cell Culture", Korea Ginseng & Tabacco Research Institute, 1995, pp. 71-110 (With English translation of the summary).

* cited by examiner

*Primary Examiner* — Qiuwen Mi
(74) *Attorney, Agent, or Firm* — Cantor Colburn LLP

(57) ABSTRACT

Disclosed is to provide a composition for enhancing skin elasticity or improving skin wrinkles, which comprises a polyol as a dispersion medium, and a ginseng cell lysate dispersed in the polyol as an active ingredient. Specifically, the composition according to the present disclosure contains a polyol and all useful substances in ginseng cells dispersed in a polyol as an active ingredient, thereby exhibiting excellent skin elasticity enhancement or skin winkle improvement effects. In addition, the preparing method according to the present disclosure can effectively disperse useful substances in ginseng cells in the polyol by using a micro fluidizer, and thus can exhibit synergistic effects of useful substances in ginseng cells.

7 Claims, 2 Drawing Sheets

COMPOSITION FOR ENHANCING SKIN ELASTICITY OR IMPROVING SKIN WRINKLES COMPRISING GINSENG CELL LYSATE

CROSS-REFERENCE TO RELATED APPLICATION

This application claims the priority of Korean Patent Application No. 10-2018-0102056, filed on Aug. 29, 2018 and all the benefits accruing therefrom under 35 U.S.C. § 119, the contents of which in its entirety are herein incorporated by reference.

BACKGROUND

1. Field

The present disclosure relates to a composition for enhancing skin elasticity or improving skin wrinkles containing ginseng cell lysate.

2. Description of the Related Art

Ginseng (*Panax ginseng* C.A. Meyer) is a perennial dicotyledonous plant belonging to *Panax ginseng* (*Araliaceae*), and its roots are used for edible or medicinal purposes. Ginseng is broadly divided into wild ginseng that naturally grows wild and ginseng that can be produced through cultivation depending on the cultivation form. There are various components found in ginseng, among which polyphenol is a substance with two or more hydroxyl groups attached to a benzene ring, and is a generic term for various phenolic compounds found in plants. Phenolic compounds are known to have anti-inflammatory and antioxidant effects. Phenolic compounds of these plants are present in cell wall components and vacuoles, and it is reported that polyphenols within cell walls can be extracted during cell disruption via grinding, pressing or the like.

Ginsenosides, which are known to be a representative active substance of ginseng, are known to be present in vacuoles and starts accumulating after a cultivation period of 4-6 years when cultivated outdoors. Such ginsenosides have been reported to have useful properties such as tonic, anticancer, vaccine, anti-stress and anti-aging properties.

On the other hand, when the conventional ginseng cultivated outdoors is used as described above, there is a problem that the quality of raw materials is significantly different depending on used part, harvest time, cultivation conditions, and natural environment, etc. In addition, most cases of compositions containing the conventional ginsengs or ginseng cells use the extract form using an organic solvent. In particular, the organic solvent extract has been used since the focus is on ginsenoside extraction.

In this regard, when the ginseng cell, cultivated using tissue culture technology and not cultivated outdoors, is used as a raw material and the ginseng cell lysate is dispersed in a polyol using only a micro fluidizer in a physical method without using an extraction process using an organic solvent, it was confirmed that not only the specific active ingredients but also all the useful substances in the ginseng cell were included intactly and exhibited excellent skin elasticity and wrinkle improvement effect due to their synergistic effects.

SUMMARY

In one aspect, an object of the present disclosure is to provide a composition for enhancing skin elasticity or improving skin wrinkles, which includes the polyol and a useful substance in ginseng cells as an active ingredient.

In another aspect, an object of the present disclosure is to provide a method of directly dispersing all useful substances in ginseng cells into a polyol by using a micro fluidizer in a physical method without using an organic solvent.

In order to achieve the above objectives, one aspect of the present disclosure provides a composition for enhancing skin elasticity or improving skin wrinkles, which comprises a polyol as a dispersion medium, and a ginseng cell lysate dispersed in the polyol as an active ingredient.

In another aspect, the present disclosure provides a method for enhancing skin elasticity or improving skin wrinkles, comprising administering a composition comprising a polyol as a dispersion medium and a ginseng cell lysate dispersed in the polyol as an active ingredient to a subject in need thereof.

In another aspect, the present disclosure provides a method for enhancing skin elasticity or improving skin wrinkles comprising administering a dispersion of ginseng cell lysate to a subject in need thereof, wherein the dispersion of ginseng cell lysate is obtained by dispersing the ginseng cell lysate in a polyol as a dispersion medium.

In another aspect, the present disclosure provides a method for preparing a composition for enhancing skin elasticity or improving skin wrinkles, which includes dispersing ginseng cells in a polyol using a micro fluidizer.

DETAILED DESCRIPTION

Hereinafter, the present disclosure will be described in detail.

As used herein, the term "ginseng cell" means that obtained by proliferating the callus derived from any one or more specific tissues and organs of ginseng using a bioreactor.

As used herein, the term "ginseng cell lysate" refers to all useful substances present in ginseng cells that can be released due to the rupturing of cell membranes of ginseng cells.

Figure 1:
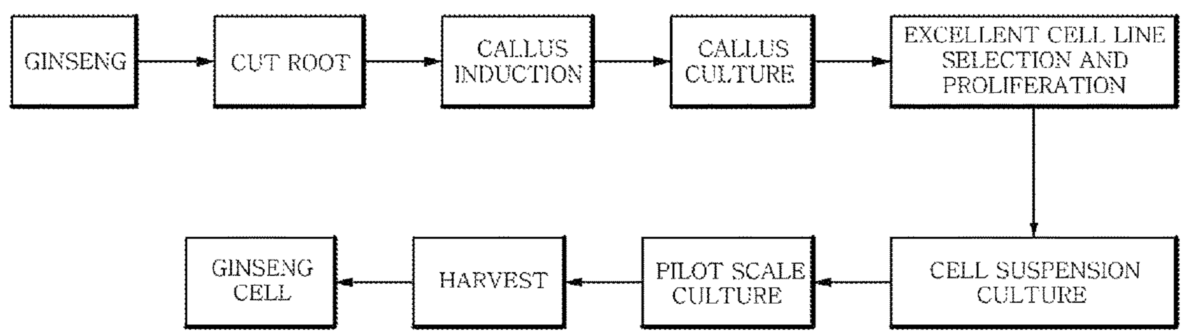
FIG. 1 is a mimetic diagram illustrating a simplified process of a ginseng cell culture according to an embodiment of the present disclosure.

As used herein, the term "ginseng cell culture" refers to a technology in which a callus is induced by extracting any one or more of specific tissues and organs of ginseng, aseptically culturing them using nutrient-containing culture medium in vitro to induce callus, and proliferating the induced callus. The simplified process of ginseng cell culture is shown in FIG. 1. Such a method of culturing ginseng cells may be referred to as plant explantation, tissue culture, in-vitro culture, aseptic culture, or plant stem cell culture.

As used herein, "in-vitro culture" is aseptically cultured in a closed space using a nutrient-containing culture medium. This is distinct from cultivating plants in outdoors.

In one aspect, the present disclosure relates to a composition for enhancing skin elasticity or improving skin wrinkles, which includes a polyol as a dispersion medium, and a ginseng cell lysate dispersed in the polyol as an active ingredient.

In another aspect, the present disclosure relates to a method for enhancing skin elasticity or improving skin wrinkles, comprising administering a composition comprising a polyol as a dispersion medium and a ginseng cell lysate dispersed in the polyol as an active ingredient to a subject in need thereof.

In another aspect, the present disclosure relates to a method for enhancing skin elasticity or improving skin wrinkles comprising administering a dispersion of ginseng cell lysate to a subject in need thereof, wherein the dispersion of ginseng cell lysate is obtained by dispersing the ginseng cell lysate in a polyol as a dispersion medium.

In one embodiment, the polyol may be one or more selected from the group consisting of butylene glycol, propane diol, propylene glycol, dipropylene glycol, isopropylene glycol, pentylene glycol, hexylene glycol, polyethylene glycol, sorbitol, glycerin and glycerol, but not limited to, and it is preferably 1,3-butylene glycol.

In one embodiment, the ginseng cell may be a ginseng root-derived cell. That is, it may be a callus cell derived from ginseng roots through tissue culture. Specifically, it may be cell mass produced by inducing callus from ginseng roots and proliferating through a bioreactor using a stable callus cell line among induced calluses.

In one embodiment, the culture medium may be MS medium (Murashige and Skoog medium). Specifically, ¼MS medium, ½MS medium, ¾MS medium, 1MS medium or 2MS medium may be used depending on the concentration of minerals in the medium. In addition, the culture medium may be added with 1-5% of sugar as an energy source, and a plant growth regulator may be added depending on the purpose. The plant growth regulator may be, for example, 2,4-D (2,4-dichlorophenoxyacetic acid).

In one embodiment, the culture medium may be used through a sterilization process. Specifically, the pH of the medium may be adjusted to 5 to 6, followed by sterilization at a temperature of 115° C. to 125° C. and at 1.0 to 1.5 atmospheric pressure.

In one embodiment, the ginseng cell proliferation may be proliferated at a temperature of 20° C. to 25° C., and preferably at a temperature of 20° C. to 22° C.

In one embodiment, the ginseng cell proliferation may be proliferated under light or dark conditions, and preferably under a dark condition.

In one embodiment, the ginseng cell proliferation may be proliferated in an enclosed bioreactor.

In one embodiment, the ginseng cell proliferation may be carried out under an air supply amount condition of 0.01 vvm to 1.0 vvm. Specifically, the air supply amount may be 0.01 vvm or higher, 0.02 vvm or higher, 0.03 vvm or higher, 0.04 vvm or higher, 0.05 vvm or higher, 0.06 vvm or higher, 0.07 vvm or higher, 0.08 vvm or higher, 0.09 vvm or higher or 0.1 vvm or higher. It addition, the air supply amount may be 1 vvm or less, 0.9 vvm or less, 0.8 vvm or less, 0.7 vvm or less, 0.6 vvm or less, 0.5 vvm or less, 0.4 vvm or less, 0.3 vvm or less, 0.2 vvm or less, 0.15 vvm or less, 0.14 vvm or less, 0.13 vvm or less, 0.12 vvm or less, or 0.11 vvm or less. Preferably, the air supply amount may be 0.08 vvm to 0.12 vvm.

In one embodiment, the composition of the air may be the same as the composition of the atmosphere.

In one embodiment, the air supply may be provided to the interior of the bioreactor after passing through at least one of an air compressor, a filter, and an air dryer. Specifically, the air may sequentially pass an air compressor capable of condensing compressed air, a filter capable of removing impurities, an air dryer, or the like to maintain a constant temperature, and then supplied to the interior of the bioreactor using an air conditioner.

The present disclosure may use ginseng cells having uniform quality throughout the year as a raw material by using ginseng root callus cells derived from ginseng roots via a tissue culture process as described above.

In one embodiment, the ginseng cell may be frozen at a temperature between −100° C. and −50° C. In one embodiment, the ginseng cell may be frozen at −100° C. or higher, −95° C. or higher, −90° C. or higher, −85° C. or higher, −80° C. or higher, −75° C. or higher, −70° C. or higher, −65° C. or higher or −60° C. or higher, or −55° C. or higher, and −50° C. or lower, −55° C. or lower, −60° C. or lower, −65° C. or lower, −70° C. or lower, −75° C. or lower, −80° C. or lower, −85° C. or lower, −90° C. or lower, or −95° C. or lower. By using the ginseng cells frozen in the above temperature range, the freshness of the ginseng cells may be maintained and the extraction efficiency of useful substances in the ginseng cells due to the rupturing of the cell membranes by congelation may be increased.

In one embodiment, the ginseng cell lysate may be dispersed in the polyol. In one embodiment, by dispersing the ginseng cells in the polyol using a micro fluidizer, useful substances in the ginseng cells, that is, ginseng cell lysate may be dispersed in the polyol.

In one embodiment, the dispersion may be performed under a pressure condition of 90 to 100 Mpa. Specifically, the dispersion may be performed under a pressure condition of 90 Mpa or more, 91 Mpa or more, 92 Mpa or more, 93 Mpa or more, 94 Mpa or more, 95 Mpa or more, 96 Mpa or more, 97 Mpa or more, 98 Mpa or more or 99 Mpa or more, and may be performed under a pressure condition of 100 Mpa or less, 99 Mpa or less, 98 Mpa or less, 97 MPa or less, 96 Mpa or less, 95 Mpa or less, 94 Mpa or less, 93 Mpa or less, 92 Mpa or less or 91 Mpa or less.

In one embodiment, the dispersion may be performed under a temperature condition of 10° C. to 30° C. Specifically, the dispersion may be performed under a temperature condition of 10° C. or higher, 12° C. or higher, 14° C. or higher, 16° C. or higher, 18° C. or higher, 20° C. or higher, 22° C. or higher, 24° C. or higher, 26° C. or higher or 28° C. or higher, and may be performed under a temperature condition of 30° C. or less, 28° C. or less, 26° C. or less, 24° C. or less, 22° C. or less, 20° C. or less, 18° C. or less, 16° C. or less, 14° C. or less or 12° C. or less.

In one embodiment, the dispersion may be performed for 1 to 5 hours. Specifically, the dispersion may be performed for 1 hour or more, 2 hours or more, 3 hours or more, 4 hours or more, 5 hours or less, 4 hours or less, 3 hours or less or 2 hours or less.

As described above, by dispersing ginseng cells under high pressure and low temperature conditions for a short time, the cell membrane is more likely to rupture and the intracellular useful substances may not be destroyed by heat, so that the extraction efficiency of useful substances in ginseng cells may be further increased. That is, the amount of the ginseng cell lysate dispersed in the polyol may increase.

In one embodiment, for the desired effect, the polyol and the ginseng cell lysate may be contained in an amount of 0.1 to 10% by weight based on the total weight of the composition. In one embodiment, the content of the polyol and ginseng cell lysate based on the total weight of the composition may be at least 0.1 wt %, at least 0.5 wt %, at least 1.0 wt %, at least 1.5 wt %, at least 2.0 wt %, at least 2.5 wt %, at least 3.0 wt %, at least 4.0 wt %, at least 5.0 wt %, at least 6.0 wt %, at least 7.0 wt %, at least 8.0 wt %, or at least 9.0 wt %, and not more than 10 wt %, not more than 9.0 wt %, not more than 8.0 wt %, not more than 7.0 wt %, not more than 6.0 wt %, not more than 5.0 wt %, not more than 4.0 wt %, not more than 3.0 wt %, not more than 2.5 wt %, not more than 2.0 wt %, not more than 1.5 wt %, not more than 1.0 wt %, or not more than 0.5 wt %.

In one embodiment, the composition may be a food composition.

Formulations of the food composition include, for example, tablets, granules, pills, powders, liquid preparations such as drinks, caramels, gels, bars, tea bags or the like, but are not particularly limited thereto. The food composition of each formulation may be blended by appropriately selecting the ingredients commonly used in the pertinent field in addition to active ingredients by those skilled in the pertinent field without difficulty depending on the formulation or purpose of use. A synergic effect may be achieved when the composition is applied concurrently with other raw materials. The food may also be a health functional food.

The composition may be administered by various methods such as simple ingestion, drinking, injection administration, spray administration, squeeze administration, or the like.

In the food composition according to one aspect of the present disclosure, the determination of the dosage of the active ingredient is within the level of those skilled in the pertinent field and may vary depending on various factors such as age, health condition, and complication of the subject to be administered.

The food composition according to one aspect of the present disclosure may be, for example, various foodstuffs such as chewing gum, caramel product, candy, ice cream, confectionery, and the like, beverages such as soft drinks, mineral water, alcoholic beverages, and the like, and health functional foods including vitamins, minerals, and the like.

In addition to the above, the food composition according to one aspect of the present disclosure may contain various nutrients, vitamins, minerals (electrolytes), flavors such as synthetic flavorings and natural flavorings, colorants and enhancers (cheese, chocolate, and the like), pectic acid and salts thereof, alginic acid and salts thereof, organic acids, protective colloid thickeners, pH adjusting agents, stabilizers, preservatives, glycerin, alcohols, and carbonating agents used in carbonated beverages. In addition, the functional food compositions of the present disclosure may contain natural fruit juice and flesh for the production of fruit juice drinks and vegetable drinks. These components may be used independently or in combination. The proportion of such additives is not so critical, but the additives are generally contained in the range of from 0 to about 60 parts by weight per 100 parts by weight of the composition of the present disclosure.

In one embodiment, the composition may be a cosmetic composition. The formulation of the cosmetic composition is not particularly limited and may be appropriately selected depending on the purpose. For example, the cosmetic composition may be formulated into one or more selected from the group consisting of a skin lotion, a skin softener, a skin toner, an astringent, a lotion, a milk lotion, a moisturizing lotion, a nourishing lotion, a massage cream, a nourishing cream, a moisturizing cream, a hand cream, a foundation, an essence, a nourishing essence, a pack, a soap, a cleansing foam, a cleansing lotion, a cleansing cream, a body lotion, and a body cleanser, but the formulation is not limited thereto.

In a case in which the formulation of the cosmetic composition according to the present disclosure is a paste, a cream, or a gel, animal fibers, plant fibers, wax, paraffin, starch, tragacanth, cellulose derivatives, polyethylene glycol, silicone, bentonite, silica, talc, zinc oxide, or the like may be used as a carrier component.

In a case in which the formulation of the cosmetic composition according to the present disclosure is a powder or a spray, lactose, talc, silica, aluminum hydroxide, calcium silicate, or polyamide powder may be used as a carrier component, and particularly in the case of a spray, propellants such as chlorofluorohydrocarbons, propane/butane, or dimethyl ether may be further contained.

In a case in which the formulation of the cosmetic composition according to the present disclosure is a solution or an emulsion, solvents, dissolvents, or emulsifiers are used as a carrier component, and examples thereof may include water, ethanol, isopropanol, ethyl carbonate, ethyl acetate, benzyl alcohol, benzyl benzoate, propylene glycol, 1,3-butyl glycol oil, glycerol aliphatic esters, polyethylene glycol, or sorbitan fatty acid esters.

In a case in which the formulation of the cosmetic composition according to the present disclosure is a suspension, liquid diluents such as water, ethanol, or propylene glycol, suspending agents such as ethoxylated isostearyl alcohol, polyoxyethylene sorbitol ester, and polyoxyethylene sorbitan ester, microcrystalline cellulose, aluminum metahydroxide, bentonite, agar, tragacanth, or the like may be used as a carrier component.

In a case in which the formulation of the cosmetic composition according to the present disclosure is a surfactant-containing cleansing, aliphatic alcohol sulfate, aliphatic alcohol ether sulfate, sulfosuccinic acid monoester, isethionate, imidazolinium derivatives, methyltaurate, sarcosinate, fatty acid amide ether sulfate, alkylamidobetaines, aliphatic alcohols, fatty acid glycerides, fatty acid diethanolamides, vegetable oils, linolenic derivatives, ethoxylated glycerol fatty acid esters, or the like may be used as a carrier component.

The cosmetic composition according to the present disclosure may further contain the functional additives and components included in the general cosmetic composition in addition to the pomegranate extract and the propolis extract. The functional additives may include the components selected from the group consisting of water-soluble vitamins, oil-soluble vitamins, polymer peptides, polymeric polysaccharides, sphingolipids and seaweed extracts.

Also, in the cosmetic composition according to the present disclosure, the components included in the general cosmetic composition may be blended in addition to the functional additives, when necessary. In addition, blending components included in addition to the above may include an oily component, a moisturizing agent, an emollient, a surfactant, organic and inorganic pigments, an organic powder, a UV absorbent, a preservative, a bactericide, an antioxidant, a plant extract, a pH regulator, an alcohol, a color, a fragrance, a blood flow stimulant, a cooling agent, a control agent, purified water, etc.

The blending amount of the above components is not particularly limited, but may be easily selected by a person skilled in the art within the scope of not impairing the objects and effects of the present disclosure. The blending amount thereof may be 0.001% to 10% by weight, and specifically 0.01% to 3% by weight based on the total weight of the composition.

In another aspect, the present disclosure may relate to a method of producing a composition for enhancing skin elasticity or improving skin wrinkles, which comprises dispersing ginseng cells in a polyol using a micro fluidizer.

The specific constitution of the production method according to the present disclosure, that is, the specific constitution regarding ginseng cell and polyol, and the pressure, temperature and time conditions of dispersion using a micro fluidizer are as mentioned above.

Hereinafter, the present disclosure will be described in further detail with reference to examples and test examples. However, the examples and test examples are given for the understanding of the disclosure of the present disclosure and not intended to limit the scope of right of the present disclosure. Modifications, substitutions, insertions, and the like that are commonly known in the technical field may be performed, and this also falls within the scope of the present disclosure.

[Preparation Example 1-1] Induction of Ginseng Cells

Ginseng (*Panax ginseng* C.A. Meyer) roots were washed three times with sterile water after surface sterilization with 70% ethanol for 30 seconds and 2% sodium hypochlorite solution for 20 minutes. Thereafter, the roots were cut into small slices, and the slices were inoculated on an MS medium (Duchefa, The Netherlands) containing 1.0 mg/L of 2,4-dichlorophenoxyacetic acid (Duchefa, The Netherlands), 3% of sucrose, and 0.23% of gelrite (Duchefa, The Netherlands). The callus was induced for 4 to 6 weeks under the dark condition that maintains 21±1° C. The induced callus was maintained and proliferated at the intervals of 3 weeks under the dark condition that maintains 21±1° C. using the same medium to mass produce ginseng cells.

[Preparation Example 1-2] Ginseng Cell Proliferation Using Bioreactor

The ginseng cells induced according to Preparation Example 1-1 were grown in a Bulb Type bioreactor having an air volume of 3 L to 10 L using the same medium as that used in Preparation Example 1-1 at intervals of 3 weeks. The culture was carried out by inoculating the ginseng cell from Preparation Example 1-1 at an inoculation density of 60 g/L and under the dark condition maintaining 21±1° C. The amount of air supplied was controlled according to the cell growth step in the range of 0.01 vvm to 0.1 vvm (air volume/culture volume per min) during the entire culture period. The air supplied into the bioreactor is passed through an air compressor that can condense compressed air, a filter that can remove impurities, and an air dryer in an orderly manner, and then is supplied into the bioreactor using an air conditioning system (RMA series, Dwyer Instruments Inc., USA) in order to maintain a constant temperature.

[Example 1] Preparation of Composition Using Micro Fluidizer

The ginseng cells mass-produced according to the above Production Example 1-2 were harvested and frozen at −80° C. Then, 1 kg of ginseng cells and 1 L of 1,3-butylene glycol were mixed and stirred using a homomixer (5,000 rpm, 30 minutes). Thereafter, the mixture was physically dispersed by repeating 2 to 3 times for 2 to 3 hours under a pressure condition of 100 MPa using a micro fluidizer. The mixture was stirred at room temperature for 24 hours, deodorized and filtered to prepare a composition of Example 1.

[Comparative Example 1] Preparation of Composition Using Ultra-High Pressure Extractor The composition was prepared in the same manner as in Example 1 except for using an ultra-high pressure extractor instead of a micro fluidizer and extracting the composition at 30° C. for 24 hours under a pressure condition of 80 MPa.

[Experimental Example 1] Cytotoxicity Evaluation Experiment

The cytotoxicity evaluation was performed to find a suitable concentration that does not show cytotoxicity of the compositions of Example 1 and Comparative Example 1. Specifically, HS68 cells, which are human skin fibroblasts, were seeded in a 96-well plate at a concentration of $1\times10^4$ cells/well, and then cultured in a DMEM medium (WelGene) containing 10% fetal bovine serum (FBS, WelGene) and 1% penicillin/streptomycin (WelGene) under a condition of 37° C. and 5% $CO_2$. The compositions of Example 1 and Comparative Example 1 were dissolved in distilled water and diluted to 250 ppm and 500 ppm, respectively. Then, the compositions were treated with cells, cultured for 24 hours, washed with DPBS (Dulbecco's Phosphate-Buffered Saline), replaced with a culture medium containing 10% EZ-Cytox solution, and cultured under a condition of 37° C. and 5% $CO_2$. Then, the absorbance was measured at 450 nm with an ELISA reader (Infinite M200 Pro, Tecan). The results are shown in Table 1 below.

TABLE 1

| | Control group | Example 1 (ppm) | | Comparative Example 1 (ppm) | |
|---|---|---|---|---|---|
| | (Untreated) | 250 | 500 | 250 | 500 |
| Cell viability (%) | 100.00 ± 1.00 | 101.90 ± 4.27 | 100.39 ± 5.03 | 99.16 ± 3.89 | 105.50 ± 4.50 |

From the results shown in Table 1 above, it was confirmed that the cell viability was 90% or more in all the concentration (250 ppm, 500 ppm) groups of Example 1 and Comparative Example 1, and that no cytotoxicity was observed. Accordingly, in Experimental Example 2, the evaluation was performed while setting the concentration to 500 ppm or less.

[Experimental Example 2] Evaluation Experiment of the Inhibition Effect of Collagenase (Matrix Metalloproteinase-1, MMP-1)

The MMP-1 ELISA assay was performed to confirm the effect of the composition of Example 1 and Comparative Example 1 on the inhibition of MMP-1 production, which is a skin tissue degrading enzyme, in UVB-irradiated human skin fibroblasts.

Specifically, HS68 cells, which are human skin fibroblasts, were seeded in a 48-well plate at a concentration of $2\times10^4$ cells/well, and then cultured in a DMEM medium (WelGene) containing 10% fetal bovine serum (FBS, WelGene) and 1% penicillin/streptomycin under a condition of 37° C. and 5% $CO_2$. Then, the medium was removed and washed with DPBS (Dulbecco's Phosphate-Buffered Saline). Then, the cells from Example 1 and Comparative Example 1 diluted by concentration (125 ppm, 250 ppm, 500 ppm) in a DMEM medium containing no fetal bovine serum (FBS) and pretreated for 6 hours. Then, the medium was removed and was filled with 100 μl of DPBS, and then was irradiated at UVB 30 mJ/cm$^2$. The cells from Example 1 and Comparative Example 1 were diluted by concentration (250 ppm, 500 ppm) in a DMEM medium containing no fetal bovine serum (FBS), treated and cultured for 48 hours. After collecting the medium of the cultured cells, the amount of MMP-1 secretion was measured using a human MMP-1 ELISA kit (R&D Systems), and the absorbance was measured at 450 nm using an ELISA reader (Infinite M200Pro, Tecan). The cells attached to the bottom of the plate were washed with DPBS, lysed with 1N NaOH, and the amount of protein was measured using a BCA assay (Pierce® BCA protein assay kit, Thermo Scientific). The amount of MMP-1 secretion per certain protein was corrected and expressed as a percentage (%). As a positive control group, 1 μM and 10 μM of retinoic acid (RA) were used. Statistical significance between samples was used by the student's t-test and was analyzed to be statistically significant when the p-value was 0.05 or less (* $P<0.05$,  $p<0.01$, * $p<0.001$). The results are shown in Table 2 and FIG. 2.

TABLE 2

| | Untreated control group | UVB 30 mJ/cm$^2$ | | |
|---|---|---|---|---|
| | | UVB | RA(μM) | |
| | | — | 1 | 10 |
| MMP-1 (%) | 100.00 ± 9.49 | 463.00 ± 13.67 | 351.95 ± 22.95 | 223.29 ± 114.85 |
| p-value | — | P < 0.001 | P < 0.01 | P < 0.001 |

| | UVB 30 mJ/cm$^2$ | | | | | |
|---|---|---|---|---|---|---|
| | Example 1(ppm) | | Comparative Example 1 (ppm) | | | |
| | 125 | 250 | 500 | 125 | 250 | 500 |
| MMP-1(%) | 449.53 ± 18.16 | 360.70 ± 35.52 | 325.37 ± 29.87 | 516.47 ± 29.96 | 548.83 ± 19.99 | 579.06 ± 21.58 |
| p-value | — | P < 0.01 | P < 0.01 | — | — | — |

Figure 2:
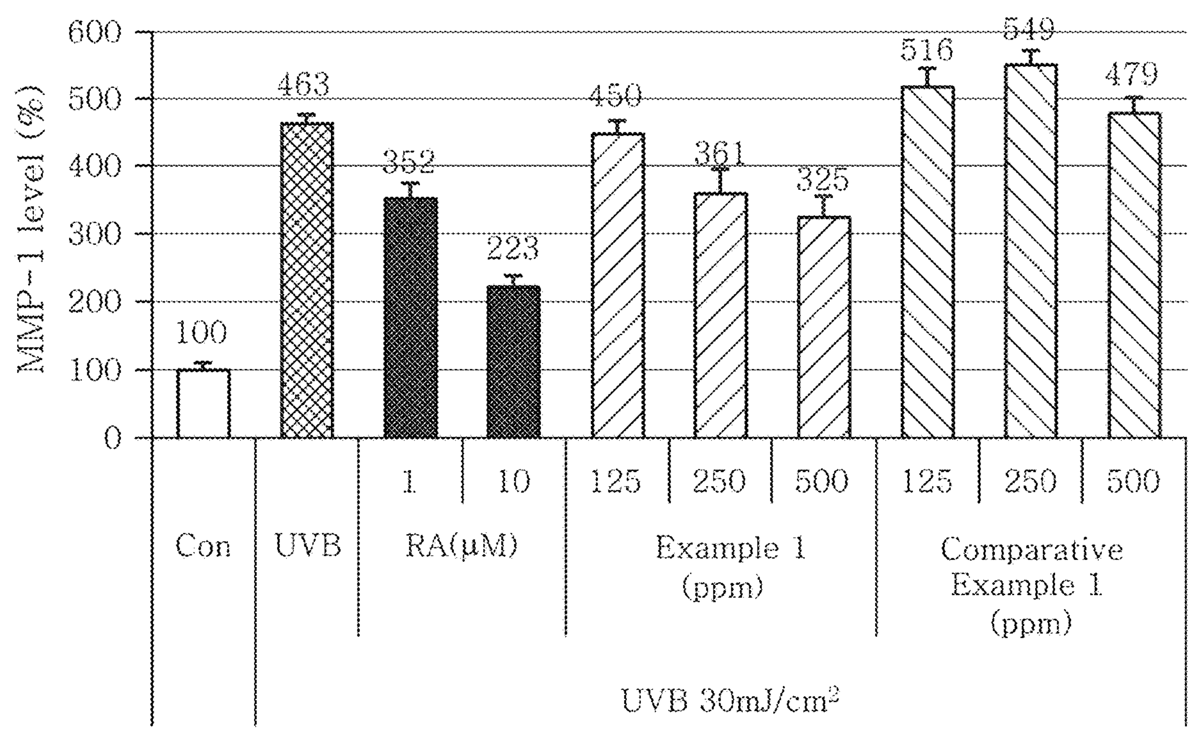
FIG. 2 shows the results of MMP1 inhibitory effect evaluation of Experimental Example 2.

From the results shown in Table 2 and FIG. 2, MMP-1 secretion increased by 363.00% ($p<0.001$) when the HS68 cells were irradiated with UVB 30 mJ/cm$^2$, 111.06% when treated with 1 μM retinoic acid, and 239.71% when treated with 10 μM of retinoic acid. It was confirmed that the secretion was significantly reduced as compared to the UVB irradiation group ($P<0.01$, $p<0.001$, respectively), In the case of Comparative Example 1, it was confirmed that the amount of MMP-1 secretion was increased as compared to the UVB irradiation group in all concentration treatments (125 ppm, 250 ppm and 500 ppm). On the other hand, in the case of Example 1 according to the present disclosure, as compared to the UVB irradiation group, the amount of MMP-1 secretion decreased by 102.30% ($p<0.01$) when treated with 250 ppm and 137.63% ($p<0.01$) when treated with 500 ppm, thereby showing a statically significant difference. In particular, when treated with 500 ppm, it was confirmed that the inhibitory effect of MMP-1 secretion similar to that when treated with 1 μM retinoic acid, a positive control group, is shown.

That is, in the case of the composition of Example 1 according to the present disclosure, by physically dispersing useful components in ginseng cells without using a conventional extraction method using organic solvent, in particular, by using a micro fluidizer which is not a ultra-high pressure extraction, the present disclosure has an excellent MMP-1 inhibitory effect due to the synergistic effect of the useful components in the ginseng cells, and thus has an effect of enhancing skin elasticity and preventing or improving skin wrinkles by inhibiting collagen reduction in the skin.

The composition according to the present disclosure contains polyol and all the useful substances in ginseng cells dispersed in polyol as an active ingredient and thus can exhibit an excellent skin elasticity enhancement effect or a skin wrinkle improvement effect.

In addition, the production method according to the present disclosure can effectively disperse useful substances in ginseng cells in polyol by using a micro fluidizer, and thus can exhibit synergistic effects of useful substances in ginseng cells.

What is claimed is:

1. A method for enhancing skin elasticity or improving skin wrinkles, consisting of administering a composition consisting of:

a dispersion medium consisting of a polyol; and a ginseng cell lysate dispersed in the polyol as an active ingredient, to a subject in need thereof, wherein the ginseng cell is frozen at a temperature of −100° C. to −50° C.

2. The method according to claim 1, wherein the polyol is one or more selected from the group consisting of butylene glycol, propanediol, propylene glycol, dipropylene glycol, isopropylene glycol, pentylene glycol, hexylene glycol, polyethylene glycol, sorbitol, and glycerin.

3. The method according to claim 2, wherein the polyol is 1,3-butylene glycol.

4. The method according to claim 1, wherein the ginseng cell is a ginseng root-derived cell.

5. The method according to claim 1, wherein the dispersion is performed at a pressure of 90 MPa to 100 MPa and a temperature of 10° C. to 30° C. for 1 to 5 hours.

6. The method according to claim 1, wherein the polyol and the ginseng cell lysate are contained in an amount of 0.1 to 10% by weight based on the total weight of the composition.

7. The method according to claim 1, wherein the composition is a food composition or a cosmetic composition.

* * * * *